(12) United States Patent
Potechin et al.

(10) Patent No.: US 12,226,512 B2
(45) Date of Patent: Feb. 18, 2025

(54) PERSONAL CARE COMPOSITIONS

(71) Applicant: Colgate-Palmolive Company, New York, NY (US)

(72) Inventors: Kathy Potechin, Short Hills, NJ (US); Min Li, Bridgewater, NJ (US); Aixing Fan, Bridgewater, NJ (US); Thomas Boyd, Metuchen, NJ (US); Melissa Moy, Staten Island, NY (US)

(73) Assignee: Colgate-Palmolive Company, New York, NY (US)

( * ) Notice: Subject to any disclaimer, the term of this patent is extended or adjusted under 35 U.S.C. 154(b) by 331 days.

(21) Appl. No.: 17/632,969

(22) PCT Filed: Aug. 10, 2020

(86) PCT No.: PCT/US2020/070386
§ 371 (c)(1),
(2) Date: Feb. 4, 2022

(87) PCT Pub. No.: WO2021/026572
PCT Pub. Date: Feb. 11, 2021

(65) Prior Publication Data
US 2022/0296491 A1    Sep. 22, 2022

Related U.S. Application Data

(60) Provisional application No. 62/884,472, filed on Aug. 8, 2019.

(51) Int. Cl.
*A61K 8/00* (2006.01)
*A61K 8/34* (2006.01)
(Continued)

(52) U.S. Cl.
CPC .............. *A61K 8/73* (2013.01); *A61K 8/345* (2013.01); *A61K 8/604* (2013.01); *A61K 8/678* (2013.01);
(Continued)

(58) Field of Classification Search
CPC ........................................................ A61K 8/37
See application file for complete search history.

(56) References Cited

U.S. PATENT DOCUMENTS 8,877,184 B2    11/2014    Potechin et al.
2014/0349902 A1*    11/2014    Allef .................... A61Q 19/10
510/491

(Continued)

FOREIGN PATENT DOCUMENTS

AU    199959577    2/2000
CN    108066195    5/2018
(Continued)

OTHER PUBLICATIONS

Kühn et al., "Characterization of Mixtures of Alkyl Polyglycosides (Plantacare) by Liquid Chromatography-Electrospray Ionization Quadrupole Time-of-Flight Mass Spectrometry", Pharmaceutical Research, vol. 21, No. 12, Dec. 2004, pp. 2347-2353.
(Continued)

*Primary Examiner* — Necholus Ogden, Jr.

(57) ABSTRACT

Described herein are personal care compositions comprising—inter alia—a gum system comprising a plurality of natural gums; a surfactant system comprising a plurality of
(Continued)

alkyl polyglucoside surfactants; and a cosmetically acceptable carrier. Methods of making and using these compositions are also described herein.

17 Claims, 4 Drawing Sheets

(51) Int. Cl.
    *A61K 8/60*     (2006.01)
    *A61K 8/67*     (2006.01)
    *A61K 8/73*     (2006.01)
    *A61K 8/92*     (2006.01)
    *A61Q 19/10*     (2006.01)

(52) U.S. Cl.
    CPC .............. *A61K 8/922* (2013.01); *A61Q 19/10* (2013.01); *A61K 2800/28* (2013.01); *A61K 2800/522* (2013.01)

(56) References Cited

U.S. PATENT DOCUMENTS

2021/0007959 A1*   1/2021   Lesch .................... A61K 8/735
2021/0371773 A1*  12/2021   Brandt ................. C12N 9/1051

FOREIGN PATENT DOCUMENTS

EP         2595599     5/2013
WO    2013/098066   7/2013

OTHER PUBLICATIONS

Anonymous, 2013, "Face Scrub", Mintel Database GNPD AN: 2159410.
Anonymous, 2018, "Body Wash", Mintel Database GNPD AN: 5550279.
Anonymous, 2019, "Gentle Shampoo for Dry and Damaged Hair", Mintel Database GNPD AN: 6367293.
Anonymous, 2019, "Shampoo & Wash Lotion", Mintel Database GNPD AN: 6735287.
International Search Report and the Written Opinion of the International Searching Authority issued in International Application PCT/US2020/070386 mailed Dec. 7, 2020.
Ware et al., 2007, "Alkylpolyglycoside: Carbohydrate Based Surfactant", Journal of Dispersion Science and Technology, 28(3):437-444.
Lin, Chen et al., "Green food and feed additives: Application and Research of Inulin," Feed Research, No. 12, (2004) pp. 16-19.

* cited by examiner

PERSONAL CARE COMPOSITIONS

CROSS-REFERENCE TO RELATED APPLICATION

This application claims the benefit of priority from U.S. Provisional Application No. 62/884,472, filed Aug. 8, 2019, the contents of which are hereby incorporated herein by reference in their entirety.

BACKGROUND

Prebiotics are well known to have beneficial effects on skin health. However, many of the currently available personal care products contain artificial ingredients; and have difficulty delivering adequate foaming and the desired prebiotic efficacy.

As such, there remains a need for natural personal care products that deliver the appropriate level of foaming, while also providing a meaningful prebiotic effect. Certain embodiments of the present invention are designed to meet these, and other, needs.

BRIEF SUMMARY

Some embodiments of the present invention provide personal care compositions comprising: a gum system comprising a plurality of natural gums; a surfactant system comprising a plurality of alkyl polyglucoside surfactants; and a cosmetically acceptable carrier.

Other embodiments of the present invention provide personal care composition comprising: a prebiotic agent; a polysaccharide gum; and a cosmetically acceptable carrier.

Further embodiments of the present invention provide methods for cleansing a keratinous surface of a subject in need thereof, comprising administering a personal care composition according to any foregoing claim, to a keratinous surface of said subject.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation.

As used herein and in the appended claims, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range.

The term "about" when referring to a number means any number within a range of 10% of the number. For example, the phrase "about 2.0 wt %" refers to a number between and including 1.800 wt % and 2.200 wt %.

All references cited herein are hereby incorporated by reference in their entireties. In the event of a conflict in a definition in the present disclosure and that of a cited reference, the present disclosure controls.

The abbreviations and symbols as used herein, unless indicated otherwise, take their ordinary meaning. The abbreviation "wt %" means percent by weight with respect to the personal care composition. The symbol "°" refers to a degree, such as a temperature degree or a degree of an angle. The symbols "h", "min", "mL", "nm", "µm" means hour, minute, milliliter, nanometer, and micrometer, respectively. The abbreviation "UV-VIS" as referring to a spectrometer or spectroscopy, means Ultraviolet-Visible. The abbreviation "rpm" means revolutions per minute.

When referring to chemical structures, and names, the symbols "C", "H", and "O" mean carbon, hydrogen, and oxygen, respectively. The symbols "—", "=" and "≡" mean single bond, double bond, and triple bond respectively.

Any member in a list of species that are used to exemplify or define a genus, may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

For readability purposes, the chemical functional groups are in their adjective form; for each of the adjective, the word "group" is assumed. For example, the adjective "alkyl" without a nouns thereafter, should be read as "an alkyl group".

The term "cosmetically acceptable carrier" as used herein refers to a physiologically acceptable medium which is compatible with keratinous substances. Suitable carriers are well known in the art and are selected based on the end-use application. Preferably, the carriers of the present invention are suitable for application to skin (e.g. in the form of creams, milks, lotions, masks, serums, hydrodispersions, foundations, cream gels, or gels etc.). Such carriers are well-known to one of ordinary skill in the art and can include one or more compatible liquid or solid filler diluent, excipient, adjuvant, additive or vehicle which are suitable for application to skin.

Personal care compositions include hair care, skin care, sun care, and nail care compositions. In some embodiments, the personal care composition is applied to the person's skin or scalp. Examples of personal care compositions include a body wash, a shower gel, a lotion, a bar soap, a soft soap, a shampoo, a hair conditioner, a sunscreen, and a cosmetic. The personal care composition may be classified and regulated by national or international regulatory agencies as a cosmetic, or as a drug.

In other embodiments, a body wash is a liquid product used for cleaning the body during showers. A body wash comprises natural and/or synthetic detergents derived from either petroleum or plant sources. A body wash has a lower pH value than soap, and is typically less drying to the skin than a soap.

In further embodiments, a shower gel is synonymous with body wash. Under an alternative embodiment, a shower gel has a higher viscosity than body wash and has a more firm consistency. A shower gel may have an ingredient that has a cooling feel.

In some embodiments, a lotion is a low-viscosity topical preparation for application to the skin. Lotions are applied to external skin with bare hands, a brush, or a clean cloth. A lotion, such as a hand lotion or a body lotion, provides smoothing, moisturizing, softening and perfuming of the skin. A lotion may be used as a medicine delivery system.

In some embodiments, the personal care composition includes a surfactant. The surfactant can be any anionic, nonionic, amphoteric, or zwitterionic surfactant, or combinations thereof. The amount of surfactant in the composition is at least 1 weight %. In other embodiments, the amount is 1 to 20 weight %, or at least 2, 4, 5, 6, 7, 8, 9, or 10 weight %.

Under various embodiments, surfactants make up 10, 20, 30, 40, or 50 percent of the personal care composition. Under an embodiment, multiple surfactants are used to achieve desired product qualities. A primary surfactant provides good foaming ability and cleaning effectiveness, while a secondary surfactant adds qualities of additional foaming, mildness to prevent irritation or over-drying of the skin. To prevent ingredients from separating, emulsifiers may be added. Additional ingredients include conditioning agents that moisturize the skin during and after product use. Ingredients, like scent in the form of essential oils or fragrance oils, and colorant in the form of water soluble dyes may also be used.

A variety of anionic surfactants can be utilized in the personal care composition including, for example, long chain alkyl ($C_6$-$C_{22}$) materials such as long chain alkyl sulfates, long chain alkyl sulfonates, long chain alkyl phosphates, long chain alkyl ether sulfates, long chain alkyl alpha olefin sulfonates, long chain alkyl taurates, long chain alkyl isethionates (SCI), long chain alkyl glyceryl ether sulfonates (AGES), sulfosuccinates and the like. These anionic surfactants can be alkoxylated, for example, ethoxylated, although alkoxylation is not required. These surfactants are typically highly water soluble as their sodium, potassium, alkyl and ammonium or alkanol ammonium containing salt form and can provide high foaming cleansing power. Other equivalent anionic surfactants may be used. In one embodiment, the anionic surfactant comprises sodium laureth sulfate, sodium pared) sulfate, and combinations thereof. Anionic surfactants can be included in any desired amount. In one embodiment, anionic surfactants are present in the composition in an amount of 0 to about 15% by weight. In one embodiment, anionic surfactants are present in an amount of about 6 to about 8% by weight.

Amphoteric surfactants may also be included in the composition. These surfactants are typically characterized by a combination of high surfactant activity, lather forming and mildness. Amphoteric surfactants include, but are not limited to derivatives of aliphatic secondary and tertiary amines in which the aliphatic radical can be straight chain or branched and wherein one of the aliphatic substituents contains about 8 to about 18 carbon atoms and one contains an anionic water solubilizing group, e.g., carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used. Examples of amphoteric surfactants include, but are not limited to, a range of betaines including, for example, high alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may be particularly useful as are those that include an amido groups such as the cocamidopropyl and cocoamidoethyl betaines. Amphoteric surfactants can be included in any desired amount. In one embodiment, amphoteric surfactants are present in the composition in an amount of 0 to about 15% by weight. In one embodiment, the amphoteric surfactants are present in the composition in an amount of about 4 to about 6% by weight.

Examples of nonionic surfactants include polysorbate 20, short and long chain alkyl glucosides having $C_8$-$C_{22}$ alkyl groups; coconut fatty acid monoethanolamides such as cocamide MEA; coconut fatty acid diethanolamides, fatty alcohol ethoxylates (alkylpolyethylene glycols); alkylphenol polyethylene glycols; alkyl mercaptan polyethylene glycols; fatty amine ethoxylates (alkylaminopotyethylene glycols); fatty acid ethoxylates (acyl polyethylene glycols); polypropylene glycol ethoxylates (for example the PLURONIC™ block copolymers commercially available from BASF); fatty acid alkylolamides, (fatty acid amide polyethylene glycols); N-alkyl-, N-alkoxypolyhydroxy fatty acid amides; sucrose esters; sorbitol esters; polyglycol ethers; and combinations thereof. Nonionic surfactants can be included in any desired amount. In one embodiment, nonionic surfactants are present in the composition in an amount of 0 to about 30% by weight, optionally from about 10 to about 25% by weight. In one embodiment, nonionic surfactants are present in the composition in an amount of about 0.5 to about 1.5% by weight.

Cationic surfactants can also be included in the composition. Examples of cationic surfactants include any quaternium or polyquatemium compound. Cationic surfactants can be included at any desired level. In one embodiment, cationic surfactants are present in the composition in an amount of 0 to about 2% by weight. In one embodiment, cationic surfactants are present in the composition in an amount of about 0.1 to about 0.3% by weight.

In some embodiments, the personal care compositions of the present invention are substantially free from anionic surfactants. In other embodiments, the personal care compositions of the present invention are free from anionic surfactants. In some embodiments, the personal care compositions of the present invention are substantially free from cationic surfactants. In other embodiments, the personal care compositions of the present invention are free from cationic surfactants.

As used herein, the term "substantially free" is intended to mean a negligible amount, for example, less than about 3 wt. % of the composition, and preferably less than 1 wt. % of the composition.

Additional ingredients may be present in the personal care composition. These include water and ingredients to thicken, preserve, emulsify, add fragrance, and color.

Skin compatible oils natural or synthetic can be included in the composition. Skin compatible oils include a range of liquid hydrocarbons, for example, linear and branched oils such as liquid paraffin, squalene, squalane, mineral oil, low viscosity synthetic hydrocarbons such as polyalphaolefins, commercially available from ExxonMobil under the trade name PURESYN PAO and polybutene under the trade name PANALANE™ or INDOPOL™, Light (low viscosity) highly branched hydrocarbon oils may also be suitable in some instances. Other useful skin compatible oils may be silicone based, for example, linear and cyclic polydimethyl siloxane, organo functional silicones (alkyl and alkyl aryl), and amino silicones. One or more natural skin compatible oils of vegetable origin can be included in the composition, for example, coconut oil, sunflower oil, sweet almond oil, avocado oil, olive oil, castor oil, jojoba oil, sesame oil, safflower oil, apricot kernel oil, soybean oil, grape seed oil, or hazelnut oil.

In other embodiments, the composition may include any of following materials in any desired amount to achieve a desired effect in the composition (amounts that can be used in some embodiments are provided): one or more alkaline salts, for example, sodium chloride, sodium sulfate, sodium carbonate, sodium bicarbonate and/or their equivalents (0 to 5% by weight); foaming agents, for example decyl glucoside, and/or their equivalents 0 to about 30% by weight, optionally from about 10 to about 25% by weight; glyceryl esters and derivatives, for example glycol distearate, and/or their equivalents (0 to 3?; by weight); sequestrants, for example, tetrasodium EDTA, and/or their equivalents (0 to 2% by weight); biocides, for example, Triclosan (2,4,4'-trichloro-2'-hydroxydiphenyl ether), DMDM hydantoin, and/or imidazolidinyl urea, and/or their equivalents (0 to 2% by weight); organic acids, for example, citric acid and/or lactic acid and/or their equivalents (0 to 2% by weight); viscosity modifiers (0 to 2% by weight); fragrances and/or perfumes (0 to 5% by weight); preservatives, for example, phenoxyethanol, parabens, pentanedial or sorbic acid (0 to 2% by weight); pearlizing agents, for example, glycol distearic esters, such as ethylene glycol distearate, but also fatty acid monoglycol esters (0 to 3% by weight); stabilizers, for example, metal salts of fatty acids, such as e.g. magnesium stearate, aluminum stearate and/or zinc stearate (0 to 2% by a weight); and dyes and pigments that are approved and suitable for cosmetic purposes.

Water may be included in the composition. Water can be included in an amount of 0 to about 90% by weight. :In one embodiment, water is present at about 50% to about 90% by weight.

In some embodiments, a moisturizing body wash composition also utilizes, as a thickening agent, a blend of PEG-150 distearate and PPG-2 hydroxyethyl cocamide for countering a decrease in viscosity associated with the concentrations of moisturizing agents utilized in sonic embodiments of the moisturizing body wash composition. This blended thickening agent allows the composition to achieve viscosities beyond those that could be achieved with conventional thickening agents, for example sodium chloride alone, and is able to achieve suitable viscosities at relatively low concentrations. The relatively low concentrations used to achieve the desired viscosities are also advantageous with respect to manufacturing processes that may be employed to manufacture the moisturizing body wash composition, thereby reducing the need for larger equipment or modifications and the capital expenditure associated with manufacturing the moisturizing body wash composition if other thickening agents were used. The PEG-150 distearate and the PPG-2 hydroxyethyl cocamide can be present in any amount to achieve a desired viscosity. In one embodiment, the amount of PEG-150 distearate in the composition is 0 to about 2% by weight. In one embodiment, the amount of PPG-2 hydroxyethyl cocamide in the composition is 0 to about 2% by weight. In one embodiment, the weight ratio of the PEG-150 distearate to the PPG-2 hydroxyethyl cocamide can be about 3:1 to about 1:3. In one embodiment the PEG-150 distearate and the PPG-2 hydroxyethyl cocamide are each present at 0.0225% by weight. The PEG-150 distearate and the PPG-2 hydroxyethyl cocamide are available as a mixture from Uniqema under the trade name PROMIDIUM™ LTS.

Microbeads may also be added to the personal care composition. Microbeads are microspheres that may added to a variety of cosmetic products for their exfoliating qualities.

Personal care composition may also contain the ingredient menthol, which gives a cooling and stimulating sensation on the skin, and some men's shower gels are also designed specifically for use on hair and body. Shower gels contain milder surfactant bases than shampoos, and some also contain gentle conditioning agents in the formula. This means that shower gels can also double as an effective and perfectly acceptable substitute to shampoo, even if they are not labelled as a hair and body wash. Washing hair with shower gel should give approximately the same result as using a moisturizing shampoo.

In certain embodiments, the present invention provides a method of treating, preventing or ameliorating a symptom associated with a disease, disorder or condition of the skin, comprising administering to the skin of a subject in need thereof, an effective amount of any one of the personal care compositions described herein.

In certain embodiments, the personal care composition has a pH of from about 3.5 to about 10.0. In other embodiments, the personal care composition has a pH of from about 3.5 to about 8.0. In some embodiments, the personal care composition has a pH of from about 3.5 to about 7.5. In other embodiments, the personal care composition has a pH of from about 3.5 to about 7.0. In further embodiments, the personal care composition has a pH of from about 3.5 to about 6.5. Still other embodiments provide personal care compositions having a pH of from about 3.5 to about 6.0. While other embodiments provide personal care compositions having a pH of from about 3.5 to about 5.5. Yet other embodiments provide personal care compositions having a pH of from about 3.5 to about 5.0. In certain embodiments, the personal care composition has a pH of from about 3.75 to about 4.5.

In certain embodiments, the personal care composition has a viscosity of from about 2,000 centipoise (cP) to about 20,000 cP, or about 3,000 cP to about 16,000 cP, or about 4,000 cP to about 12,000 cP, including all values in between these ranges.

In certain embodiments, the personal care composition is substantially free of a sulfate-containing surfactant. In certain embodiments, the personal care composition is free of a sulfate-containing surfactant, In certain embodiments, the personal care composition further comprises a cationic polymer. In certain embodiments, the cationic polymer provides conditioning benefits. In certain embodiments, the cationic polymer comprises a copolymer of acrylamide and diallyldimethylammonium chloride.

In certain embodiments, the personal care composition further comprises a prebiotic polysaccharide. In certain embodiments, the prebiotic polysaccharide comprises a fructan. In other embodiments, the prebiotic polysaccharide comprises inulin. In certain embodiments, the prebiotic polysaccharide is present in an amount of from about 0.1 wt. % to about 5 wt. %, optionally from about 0.5 wt,% to about 3 wt. %, further optionally about 2 wt. %.

Additional ingredients may be present in the personal care composition. These include water and ingredients to thicken, preserve, emulsify, add fragrance, and color.

In some embodiments, the composition can further comprise certain additives, including, for example, proteins (e.g., hydrolyzed vegetable protein, hydrolyzed wheat protein, hydrolyzed milk protein, hydrolyzed silk and hydrolyzed collagen), vitamins panthenol, biotin, vitamin E acetate, vitamin A and D palmitate), moisturizers/humectants (e.g., glycerin, propylene glycol, sodium pyroglutamic acid (also known as PCA), amino acid-based surfactants, and HLA), emollients (e.g., esters, isopropyl myristate, decyl oleate, $C_{12-15}$ alkyl benzoate), oils (e.g., coconut, jojoba., aloe vera, safflower, almond, argon, sunflower oil, avocado oil, flax seed oil), botanicals (e.g., chamomile, aloe, rosemary), as well as preservatives, dyes, pH adjusters and chelating agents.

In certain embodiments, in order to prevent ingredients from separating, emulsifiers may be added in certain embodiments, additional ingredients may include conditioning agents that moisturize the skin during and after product use. In further embodiments, ingredients, like scent in the form of essential oils or fragrance oils, and colorant in the form of water-soluble dyes may also be used.

In some embodiments, the composition may include vitamins, including but not limited. to, tocopherol, retinol, and ascorbic acid. In one embodiment, the composition may include vitamin derivatives such as ascorbyl monopalmitate, tocopheryl acetate, and Vitamin E palmitate. In one embodiment, the composition may include vitamins and vitamin derivatives.

The personal care composition may further comprise one or more fragrances. The fragrance may be present in an amount ranging from about 0.01% wt. % to about 2.0% wt. %—based on the total weight of the personal care composition—including all percentages and sub-ranges there-between. In some embodiments, the fragrance may be present in an amount ranging from about 0.4% wt. % to about 1.7% wt. %—based on the total weight of the soap composition—including all percentages and sub-ranges there-between.

Non-limiting examples of fragrances and perfumes include odor compounds selected from: 7-acetyl-1,2,3,4,5,6,7,8-octahydro-1,1,6,7-tetramethylnaphthalene, α-ionone, β-ionone, γ-ionone α-isomethylionone, methylcedrylone, methyl dihydrojasmonate, methyl 1,6,10-trimethyl-2, 5,9-cyclododecatrien-1-yl ketone, 7-acetyl-1,1,3,4,4,6-hexamethyltetralin, 4-acetyl-6-tert-butyl-1,1-dimethylindane, hydroxyphenylbutanone, benzophenone, methyl β-naphthyl ketone, 6-acetyl-1,1,2,3,3, 5-hexamethy indane, 5-acetyl-3 sopropyl-1,1,2,6-tetramethylindane, 1-dodecanal, 4-(4-hydroxy-4-rnethylpentyl)-3-cyclohexene-1-carboxaldehyde, 7-hydroxy-3,7-dimethyoctanal, 10-undecen-1-al, isohexenylcyclohexylcarboxaldehyde, formyltricyclodecane, condensation products of hydroxycitronellal and methyl anthranilate, condensation products of hydroxycitronellal and indole, condensation products of phenylacetaldehyde and indole, 2-methyl-3-(para-tert-butylphenyl)propionaldehyde, ethylvanillin, heliotropin, hexylcinnamaldehyde, amylcinnamaldehyde,2-methyl-2-(isopropylphenyl)propionaldehyde, coumarin, γ-decalactone, cyclopentadecanolide, 16-hydroxy-9-hexadecenoic acid Intone, 1,3,4,6,7,8-hexahydro-4,6,6$_2$7,8,8-hexamethy cyclopenta-γ-2-benzopyran, β-naphthol methyl ether, ambroxane, dodecahydro-3a,6,6, 9a-tetramethylnaphtho[2,1b]furan, cedrol, 5-(2,3-trimethylcyclopent-3-enyl)-3-methylpentan-2-ol, 2-ethyl-4-(2,2,3-trimethyl-3-cyclopenten-1-yl)-2-buten-1-ol, caryophyllene alcohol, tricyclodecenyl propionate, tricyclodecenyl acetate, benzyl salicylate, cedryl acetate, and tert-butylcyclohexyl acetate.

Other fragrances may include odor compounds selected from essential oils, resinoids and resins from a large number of sources, such as, for example, Peru balsam, olibanum resinoid, styrax, labdanum resin, nutmeg, cassia oil, benzoin resin, coriander, and lavandin.

Further suitable fragrances include odor compounds selected from phenylethyl alcohol, terpineol, linalool, linalyl acetate, geraniol, nerol, 2-(1,1-dimethylethyl)cyclo-hexanol acetate, benzyl acetate, and eugenol. The fragrances or perfumes can be used as single substances or in a mixture with one another.

The personal care composition may further comprise one or more colorants. The colorants may be a pigment, a dye, or mixtures thereof. Non-limiting examples of pigments include titanium dioxide, Zinc Oxide, Kaolin, Mica etc. Non-limiting examples of dyes include food dyes suitable for food, drug and cosmetic applications, and mixtures thereof. Some color agents (colorants) are known as FD&C dyes.

The colorants may be present in an amount ranging from about 0.0001% wt. % to about 0.4% wt. %—based on the total weight of the soap composition—including all percentages and sub-ranges there-between. In some embodiments, the colorants may be present in an amount ranging from about 0.0001% wt. % to about 4% wt. % based on the total weight of the personal care composition—including all percentages and sub-ranges there-between.

The personal care composition may comprise a silicon-containing component. The silicon-containing component may comprise one or more silicone oils, such as dimethicone. Dimethicone is a mixture of fully methylated linear siloxane polymers end blocked with trimethylsiloxy units. Dimethiconol is a dimethyl silicone polymer terminated with hydroxyl groups. These silicone oils are relatively non-volatile liquids.

The silicone oil may be copolymer, such as dimethicone-copolyol. Dimethicone-copolyol may comprise one or more copolymer of dimethylpolysiloxane with polyoxyethylene and/or polyoxypropylene side chains. The copolymer may alternatively comprise phosphated silicone polymers of the above-cited patent can be called dimethicone copolyol phosphates, in terms of chemical structure, the phosphate group forms the terminus of the polyoxyalkylene side chain, and the end hydroxyl has been converted to an ester linkage to the phosphate group.

In some embodiments, the present invention provides a personal care composition comprising: a gum system comprising a plurality of natural gums; a surfactant system comprising a plurality of alkyl polyglucoside surfactants; and a cosmetically acceptable carrier.

In some embodiments, the natural gums are selected from: xanthan gum; carrageenan; agar; an alginate (e.g. alginic acid or sodium alginate); gum arabic; gum ghatti; gum tragacanth; karaya gum; guar gum; locust bean gum; acacia senegal; konjac gum; pectin; sclerotium gum; scleroglucan; beta-glucan; dammar gum; glucomannan; psyllium seed husks; tara gum; and gellan gum. In further embodiments, the natural gums are selected from: xanthan gum; carrageenan; guar gum; karaya gum; an alginate; and gum arabic. In other embodiments, the plurality of natural gums comprises two natural gums. In further embodiments, the plurality of natural gums comprises: xanthan gum and carrageenan.

In some embodiments, the gum system comprises from about 0.1 wt. % to about 3 wt. %, of the total weight of the composition. In other embodiments, the gum system comprises from about 0.5 wt. % to about 2 wt. %, of the total weight of the composition. Still further embodiments provide personal care compositions wherein the gum system comprises from about 0.75 wt. % to about 1.5 wt. %, of the total weight of the composition. While other embodiments provide personal care compositions wherein the gum system comprises about 1 wt. %, of the total weight of the composition.

In other embodiments, the plurality of alkyl polyglucoside surfactants comprises a first alkyl polyglucoside surfactant and a second alkyl polyglucoside surfactant. In some embodiments, the first alkyl polyglucoside surfaaant and the second alkyl polyglucoside surfactant are present in a weight ratio of from about 6:1. Still further embodiments provide personal care compositions wherein the first alkyl polyglucoside surfactant and the second alkyl polyglucoside surfactant are present in a weight ratio of from about 4:1 to about 1:4. Other embodiments provide personal care compositions wherein the first alkyl polyglucoside surfactant and the second alkyl polyglucoside surfactant are present in a weight ratio of from about 3.5:1 to about 1:3.6. Yet other embodiments provide personal care compositions wherein the first alkyl polyglucoside surfactant and the second alkyl polyglucoside surfactant are present in a weight ratio of from about 3:1 to about 1:3. In some embodiments, the first alkyl polyglucoside surfactant and the second alkyl polyglucoside surfactant are present in a weight ratio of about 2.5:1 to 1:2.5. Still other embodiments provide personal care compositions wherein the first alkyl polyglucoside surfactant and the second alkyl polyglucoside surfactant are present in a weight ratio of from about 2.5:1 to about 1:2.5. Still further embodiments provide personal care compositions wherein the first alkyl polyglucoside surfactant and the second alkyl polyglucoside surfactant are present in a weight ratio of from about 2:1 to about 1:1.

In certain embodiments, the plurality of alkyl polyglucoside surfactants are selected from: decyl glucoside; caprylyl glucoside; capryl glucoside; lauryl glucoside; coco-glucoside; and mixtures thereof (e.g. caprylyl/capryl glucoside). In various embodiments, the plurality of alkyl polyglucoside surfactants comprises: decyl glucoside and caprylyl/capryl glucoside.

Other embodiments of the present invention a personal care composition further comprising a prebiotic agent. In further embodiments, the prebiotic agent comprises inulin.

In some embodiments, the compositions described herein further comprise an emollient, In some embodiments, the emollient comprises sunflower seed oil.

Still further embodiments provide compositions that further comprise an antioxidant. In certain embodiments, the antioxidant is selected from: vitamin A, niacinamide; vitamin C; vitamin E; a polyphenol; resveratrol; co-enzyme Q10; a flavonoid; and a combination of two or more thereof.

Still further embodiments provide personal care compositions comprising a prebiotic agent; a polysaccharide gum; and a cosmetically acceptable carrier.

Yet other embodiments provide a method for cleansing a keratinous surface of a subject in need thereof, comprising administering a personal care composition according to any foregoing claim, to a keratinous surface of said subject. Some embodiments provide methods that further comprise the step of rinsing the keratinous surface to remove at least a portion of the personal care composition, Still further embodiments provide methods that further comprise the step of rinsing the keratinous surface until the personal care composition is substantially removed therefrom. In some embodiments, the keratinous surface is selected from: hair; skin; nails; and a combination of two or more thereof.

In some embodiments, the present invention provides personal care compositions comprising: a humectant (e.g. from about 5-10%, or about 6% glycerin); a natural gum system (e.g., from about 0.5 to 2%, or 1% of a mixture of xanthan (e.g. 0.7%) and carrageenan (e.g., 0.3%)); a polyglucoside surfactant system (e.g., from about 15-25%, or about 22% of a mixture of Caprylyl/Capryl Glucoside (16.95%) and decyl glucoside (4.84%)); a skin compatible oil (e.g., from about 3 to 4% of sunflower oil); a prebiotic agent (e.g., about 2%); an antioxidant (e.g., from about 0.01 to about 0.5% of Vitamin E); an organic acid (e.g., a mixture of lactic acid (from about 0.1 to about 1%) and citric acid (from about 0.5% to about 2%)); and water.

In other embodiments, the present invention provides personal care compositions comprising: a humectant (e.g. from about 5-10%, or about 6% glycerin); a natural gum system (e.g., from about 0.5 to 2%, or l% of a mixture of xanthan (e.g. 0.7%) and carrageenan (e.g., 0.3%)); a polyglucoside surfactant system (e.g., from about 10-15%, or about 14% of a mixture of Caprylyl/Capryl Glucoside (~10%) and decyl glucoside (3%); a skin compatible oil (e.g., from about 3 to 4% of sunflower oil); a prebiotic agent (e.g., about 2%); an antioxidant (e.g., from about 0.01 to about 0.5% of Vitamin E); an organic acid (e.g., a mixture of lactic acid (from about 0.1 to about 1%) and citric acid (from about 0.5% to about 2%)); and water.

The present invention is also directed to a method of cleansing a keratinous substance comprising applying a personal care composition according to any one of embodiments described to the skin of a subject in need thereof. The spreading of the personal care composition may be done by hand, or it may be done by an instrument such as a glove, pouf or a piece of cloth. In certain embodiments of the method, the keratinous surface is selected from: skin, hair; nails; and a combination of two or more thereof. In certain embodiments of the method, the method further comprises rinsing the skin to which the personal care composition was applied.

In some embodiments, the method of applying the personal care composition may leave behind a film. The thickness of the film depends on other parts of the formulation, but for a lotion, the thickness will be comparable to the thicknesses of other lotions, body washes, or deodorants. For those embodiments wherein the personal care composition is a lotion, the thickness is about 50 μm.

In some embodiments, the present invention is also directed to a method of treating, preventing or ameliorating a symptom associated with a disease, disorder or condition of a keratinous substance, comprising applying a personal care composition according to any one of the embodiments described herein to a keratinous substance of a subject in need thereof. In some embodiments, the disease, disorder or condition of a keratinous substance is selected from: inflammation; irritation; dryness; and the like.

In certain embodiments, the present invention is also directed to a method of cleansing a keratinous substance comprising applying a personal care composition according to any of the embodiments provided herein to a keratinous substance of a subject in need thereof in certain embodiments, the keratinous substance is selected from: skin, hair, nails, and a combination of two or more thereof. In certain embodiments, the method further comprises rinsing the personal care composition from the keratinous substance to which it is applied.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1: Exemplary and Comparative Compositions

Unless otherwise specified, all percentages and amounts expressed herein and elsewhere in the specification should be understood to refer to percentages by weight. The amounts given are based on the active weight of the material.

TABLE 1

Body Wash (Ex. I)

| Ingredient | w/w % |
| --- | --- |
| Water | 50-70 |
| Glycerin | 5-10 |
| Xanthan Gum | 0.1-2 |
| Carrageenan | 0.1-2 |
| Caprylyl/Capryl Glucoside | 0.1-20 |
| Decyl Glucoside | 0.1-20 |
| Sunflower Oil | 0.1-5 |
| Vitamin E | 0.01-1 |
| Inulin | 0-10 |
| Fragrance | 0.1-2 |
| Lactic Acid | 0.05-1 |
| Citric Acid | 0.05-2 |

TABLE 2

Liquid Hand Soap (Ex. II)

| Ingredient | w/w % |
| --- | --- |
| Water | 60-80 |
| Glycerin (USP & EP) | 5-10 |
| Xanthan Gum | 0.1-2 |
| Carrageenan | 0.1-2 |
| Caprylyl/Capryl Glucoside | 0.1-20 |
| Decyl Glucoside | 0.1-10 |
| Sunflower Oil | 0.1-5 |
| Vitamin E | 0.10 |
| Inulin | 0-10 |
| Fragrance | 0.1-2 |
| Lactic Acid | 0.1-2 |
| Citric Acid | 0.1-2 |

TABLE 3

Body Wash and Liquid Hand Soaps (Ex. III-IX)

| Ingredients | w/w % |
| --- | --- |
| Water | 60-80 |
| D-Glucopyranose, oligomeric, decyl octyl glycosides | 5-20 |
| Glycerin | 2-10 |
| Decyl Glucoside | 0.1-10 |
| D-Glucopryonase, oligomeric, C10-C16-alkyl glycosides | 0.1-10 |
| Sunflower Seed Oil | 0.1-7 |
| Sodium Chloride | 0.1-5 |
| Xanthan Gum | 0.1-2 |
| Citric Acid | 0.1-2 |
| Lactic Acid | 0.1-2 |
| Carrageenan | 0.05-2 |
| Vitamin E | 0.01-2 |
| Soybean Oil | 0.01-0.5 |
| Inulin | 0-10 |
| Minors (e.g. fragrance, colorants, etc.) | 0.1-2 |

TABLE 4

Comparative Example (Comp. Ex. I)

Ingredients

Water
Lauryl Glucoside
Decyl Glucoside
Sucrose Laurate
Coco-Glucoside
Glyceryl Oleate
Citric Acid
Glycerin
Sodium Chloride
Tocopherol
Hydrogenated Palm Glycerides Citrate
Lecithin
Ascorbyl Palmitate
Potassium Sorbate
Fragrance
Phenoxyethanol
Citral
Eugenol
Limonene
Linalool

TABLE 5

Comparative Example (Comp. Ex. II): Conventional Body Wash
Ingredients

- Aqua/Water/Eau
- Sodium C12-13 Pareth Sulfate
- Cocamidopropyl Betaine
- Parfum/Fragrance
- Sodium Chloride
- Cocamide MEA
- Sodium Salicylate
- Sodium Benzoate
- Citric Acid
- Polyquaternium-7
- Tetrasodium EDTA
- Yellow 5
- Blue 1

TABLE 6

Comparative Example (Comp. Ex. III)
Ingredient

- Water
- Decyl Glucoside
- Glycerin
- Coco-glucoside
- Sunflower Oil
- Sodium Gluconate
- Fragrance
- Xanthan Gum
- Sodium lactate
- Citric Acid
- Lactic Acid
- Carrageenan
- Vitamin E
- Soybean Oil

TABLE 7

Comparative Example (Comp. Ex. IV)
Ingredient

Water
Cocamidopropyl Hydroxysultaine
Sodium Methyl 2-Sulfolaurate
Glycerin
*Lavandula Angustifolia* (Lavender) Oil
*Citrus Aurantium Dulcis* (Orange) Peel Oil
Fragrance
*Olea Europaea* (Olive) Fruit Oil
*Aloe Barbadensis* Leaf Juice
Disodium 2-Sulfolaurate
Citric Acid
Sodium Chloride
Potassium Sorbate
Sodium Benzoate

TABLE 8

Comparative Example (Comp. Ex. V)
Ingredient

- Water
- Cocamidopropyl Hydroxysultaine
- Sodium Methyl 2-Sulfolaurate
- Glycerin
- *Lavandula Angustifolia* (Lavender) Oil
- *Citrus Aurantium Dulcis* (Orange) Peel Oil
- Fragrance
- *Olea Europaea* (Olive) Fruit Oil
- *Aloe Barbadensis* Leaf Juice
- Disodium 2-Sulfolaurate
- Citric Acid
- Sodium Chloride
- Potassium Sorbate
- Sodium Benzoate Tables 9, 10 and 11 (below) represent exemplary body wash and liquid hand soap formulations with caprylyl/capryl glucoside alone, decyl glucoside alone and with differing ratios of a combination of caprylyl/capryl glucoside and decyl glucoside from 3.5:1 to 1:3.6.

TABLE 9

| Example | Coco Glucoside w/w % | Caprylyl/ Capryl Glucoside w/w % | Decyl Glucoside w/w % | Ratio (Approximation) |
|---|---|---|---|---|
| Ex. III | 14.42 | — | 11.0 | 1.3:1 Coco Glucoside:Decyl Glucoside |
| Ex. IV | — | 16.95 | 4.84 | 3.5:1 Caprylyl/Capryl Glucoside:Decyl Glucoside |
| Ex. V | — | 20.99 | — | 1:0 Caprylyl/Capryl Glucoside:Decyl Glucoside |
| Ex. VI | — | 14.69 | 7.54 | 1.95:1 Carpylyl/Capryl Glucoside:Decyl Glucoside |
| Ex. VII | — | 10.49 | 12.57 | 1:12 Carpylyl/Capryl Glucoside:Decyl Glucoside |
| Ex. VIII | — | 5.25 | 18.66 | 1:3.5 Carpylyl/Capryl Glucoside:Decyl Glucoside |
| Ex. IX | — | — | 25.15 | 0:1 Carpylyl/Capryl Glucoside:Decyl Glucoside |

TABLE 10

Exemplary Body Washes

| | Examples | | | | | |
|---|---|---|---|---|---|---|
| | X | XI | XII | XIII | XIV | XV |
| Ratio: Caprylyl/Capryl Glucoside:Decyl Glucoside | 3.5:1 | 1:0 | 1:1.2 | 1:3.6 | 2.5:1 | 0:1 |
| Ingredient | w/w % | w/w % | w/w % | w/w % | w/w % | w/w % |
| Deionized Water | 63.16 | 64.81 | 62.74 | 61.69 | 63.77 | 60.65 |
| Glycerin (USP Kosher) | 6.00 | 6.00 | 6.00 | 6.00 | 6.00 | 6.00 |
| Xanthan Gum (Xantural 75) | 0.70 | 0.70 | 0.70 | 0.70 | 0.70 | 0.70 |
| Carrageenan (Genuvisco CG-131) | 0.30 | 0.30 | 0.30 | 0.30 | 0.30 | 0.30 |
| Caprylyl/Capryl Glucoside (Plantaren 810UP) | 16.95 | 20.99 | 10.49 | 5.25 | 15.74 | 0.00 |
| Decyl Glucoside (Plantaren 2000 NUP) | 4.84 | 0.00 | 12.57 | 18.86 | 6.29 | 25.15 |
| Sunflower Oil (Lipovol) | 3.40 | 3.40 | 3.40 | 3.40 | 3.40 | 3.40 |
| Vitamin E | 0.10 | 0.10 | 0.10 | 0.10 | 0.10 | 0.10 |
| Inulin | 2.00 | 2.00 | 2.00 | 2.00 | 2.00 | 2.00 |
| Lactic Acid (Purac 80) | 0.70 | 0.70 | 0.70 | 0.70 | 0.70 | 0.70 |
| Citric Acid (50% solution) | 1.00 | 1.00 | 1.00 | 1.00 | 1.00 | 1.00 |

TABLE 11

Exemplary Liquid Hand Soaps

| | Examples | | | | | |
|---|---|---|---|---|---|---|
| | XVI | XVII | XVIII | XIX | XX | XXI |
| Ratio: Caprylyl/Capryl Glucoside:Decyl Glucoside | 3.5:1 | 1:0 | 1:1.2 | 1:3.6 | 2.5:1 | 0:1 |
| Ingredient | w/w % | w/w % | w/w % | w/w % | w/w % | w/w % |
| Deionized Water | 72.58 | 73.91 | 72.66 | 72.04 | 73.29 | 71.42 |
| Glycerin (USP Kosher) | 6.00 | 6.00 | 6.00 | 6.00 | 6.00 | 6.00 |
| Xanthan Gum (Xantural 75) | 0.70 | 0.70 | 0.70 | 0.70 | 0.70 | 0.70 |
| Carrageenan (Genuvisco CG-131) | 0.30 | 0.30 | 0.30 | 0.30 | 0.30 | 0.30 |
| Caprylyl/Capryl Glucoside (Plantaren 810UP) | 10.17 | 12.59 | 6.30 | 3.15 | 9.44 | 0.00 |
| Decyl Glucoside (Plantaren 2000 NUP) | 2.90 | 0.00 | 7.54 | 11.31 | 3.77 | 15.08 |
| Sunflower Oil (Lipovol) | 3.40 | 3.40 | 3.40 | 3.40 | 3.40 | 3.40 |
| Vitamin E | 0.10 | 0.10 | 0.10 | 0.10 | 0.10 | 0.10 |
| Inulin | 2.00 | 2.00 | 2.00 | 2.00 | 2.00 | 2.00 |
| Lactic Acid (Purac 80) | 0.40 | 0.40 | 0.40 | 0.40 | 0.40 | 0.40 |
| Citric Acid (50% solution) | 0.60 | 0.60 | 0.60 | 0.60 | 0.60 | 0.60 |

The compositions described herein can be made by conventional techniques generally known to those skilled in the art. For example, main water is added to a vessel equipped with a center turbine agitation, the prebiotic (e.g. inulin) is premixed with 4-5% water; and the gums are premixed with glycerin. The premixes are then added to the main batch and heated to about 60° C. After mixture cools to about 40° C. or less, the caprylyl/capryl glucoside and decyl glucoside are added. Oils and antioxidants are then slowly added, followed by fragrance. The organic acids are then added and titrated to achieve the desired pH of about 4.

Example 2

Foam testing or characterization can be done using various methods. For example, foam structure and characterization can be made using a Dynamic Foam Analyzer Model DFA 100 from Kruss USA, Matthews, N.C.

Foam profiles can also be measured using a mechanical cylindrical shake foam method, such as a Gauer Foam Method.

Foam testing measurements were used to evaluate the foam profile of the exemplary body washes and liquid hand soaps of the present invention, as well as the comparative examples described herein. Measurements were made using a mechanical cylinder shake foam method and a Gaum Foam Height Machine available from Gaum, Inc., Robbinsville, N.J. Measurements were made for flash foam, max foam and drainage time.

Procedure: Weigh into a beaker 75 g of test body wash or liquid hand soap. Weigh 425 g of Deionized water 1000 mL glass beaker and place a 1-inch magnetic stir bar in it. Place beaker on stir/hot plate and start mixing until the body wash or liquid hand soap is fully dispersed. Mixing speed should be such that very little foam is generated, Heat solution to 41-42° C. Once solution reaches 41-42° C., the solution is prepared. The quantity made is enough to use in 3 cylinder tests. Keep sample at a constant temperature of 41-42° C. when not being used for test. Heat DI water to 45° C. Fill the 500 mL graduated cylinder completed with 45° C. DI water. Allow the DI water to sit in the graduated cylinder for a few minutes. Drain DI water from cylinder just prior to pouring the body wash solution and testing. Drain the 500 mL glass cylinder when the body wash test solution temperature is reached. When the body wash test solution reaches 41-42° C., pour 100 g of body wash test solution into 500 mL cylinder. Tilt the graduated cylinder on an angle and pour down the slide of the cylinder at a slow rate such that little to no foam is generated from the pour. Put the Teflon bar in and close with rubber stopper, Attach the 500 mL cylinder to the rotator assembly (Gaum Foam Machine) to keep the cylinder in the perpendicular plane when rotating. Rotate the cylinder a constant speed of (30 RPM) for the following cycles:

a. Flash Foam Measurement
   8 Cycles: a reading of foam volume is taken upon completion of the 8 cycles. An average and standard deviation is conducted on the 3 samples for each product.
b. Maximum Foam and Drainage Time Measurements
   12 Cycles: start timing instantly upon cycle completion. A reading of the maximum foam volume is taken upon completion of the 12 cycles for the Max Foam and the timing are stopped once the liquid portion contained in the cylinder has reached 100 mL of the drainage time.

An average and standard deviation is conducted on the 3 samples for each product. Drainage time is defined as the time measured from completion of the 12 cycles to the time at which 100 mL of liquid has drained. Drainage e is a measure of the wetness and stability of the foam.

TABLE 12

Flash Foam - 8 Cycles for Exemplary Body Washes

| Product | Trial | Solution (g) | Foam Line (mL) | Flash Foam Average (mL) | Standard Deviation |
|---|---|---|---|---|---|
| Comp. Ex. I | 1 | 100.00 | 360 | 351.67 | 7.64 |
|  | 2 | 100.07 | 350 |  |  |
|  | 3 | 100.04 | 345 |  |  |
| Comp. Ex. III | 1 | 100.02 | 380 | 381.67 | 2.89 |
|  | 2 | 100.01 | 380 |  |  |
|  | 3 | 100.22 | 385 |  |  |
| Ex. I | 1 | 100.01 | 425 | 401.67 | 20.21 |
|  | 2 | 100.04 | 390 |  |  |
|  | 3 | 100.01 | 390 |  |  |

TABLE 13

Max Foam - 12 Cycles for Exemplary Body Washes

| Product | Trial | Solution (g) | Foam Line (mL) | Flash Foam Average (mL) | Standard Deviation |
|---|---|---|---|---|---|
| Comp. Ex. I | 1 | 100.01 | 375 | 365.00 | 8.66 |
|  | 2 | 100.05 | 360 |  |  |
|  | 3 | 100.05 | 360 |  |  |
| Comp. Ex. III | 1 | 100.02 | 425 | 413.33 | 12.58 |
|  | 2 | 100.06 | 415 |  |  |
|  | 3 | 100.02 | 400 |  |  |
| Ex. I | 1 | 100.05 | 425 | 433.33 | 14.43 |
|  | 2 | 100.03 | 425 |  |  |
|  | 3 | 100.01 | 450 |  |  |

TABLE 14

Drainage Time - 12 cycles for Exemplary Body Washes

| Product | Trial | Drainage Time (hours:minute:seconds) | Average | Standard Deviation |
|---|---|---|---|---|
| Comp. Ex. I | 1 | 0:05:02 | 0:07:36 | 0:02:38 |
|  | 2 | 0:10:17 |  |  |
|  | 3 | 0:07:28 |  |  |
| Comp. Ex. III | 1 | 0:15:34 | 0:12:49 | 0:02:49 |
|  | 2 | 0:12:56 |  |  |
|  | 3 | 0:09:57 |  |  |
| Ex. I | 1 | 0:15:30 | 0:16:37 | 0:01:58 |
|  | 2 | 0:18:53 |  |  |
|  | 3 | 0:15:27 |  |  |

TABLE 15

Foam Testing for Exemplary Body Washes

| Product | Flash Foam Average (mL) (8 Cycles) | Standard Deviation | Flash Foam Average (mL) (12 Cycles) | Standard Deviation |
|---|---|---|---|---|
| Comp. Ex. III | 378.33 | 12.58 | 376.67 | 2.89 |
| Ex. III | 385.00 | 8.66 | 441.67 | 14.43 |
| Ex. X | 413.33 | 11.55 | 446.67 | 5.77 |
| Ex. XI | 400.00 | 0.00 | 446.67 | 20.82 |
| Ex. XV | 385.00 | 8.66 | 445.00 | 15.00 |
| Ex. XII | 433.33 | 5.77 | 491.67 | 55.30 |
| Ex. XIII | 406.67 | 10.41 | 435.00 | 5.00 |
| Ex. XIV | 400.00 | 10.00 | 446.67 | 38.84 |

TABLE 16

Drainage Time (12 Cycles) for Exemplary Body Washes

| Product | Drainage Time (hours:minute:seconds) (12 Cycles) | Standard Deviation |
|---|---|---|
| Comp. Ex. III | 0:06:27 | 0:01:05 |
| Ex. III | 0:09:41 | 0:01:37 |
| Ex. X | 0:15:55 | 0:01:37 |
| Ex. XI | 0:12:26 | 0:04:54 |
| Ex. XV | 0:12:30 | 0:00:24 |
| Ex. XH | 0:11:08 | 0:02:54 |
| Ex. XIII | 0:10:44 | 0:01:50 |
| Ex. XIV | 0:08:07 | 0:02:22 |

TABLE 17

Foam testing for Exemplary/Liquid Hand Soaps

| Product | Flash Foam Average (mL) (8 Cycles) | Standard Deviation | Flash Foam Average (mL) (12 Cycles) | Standard Deviation |
|---|---|---|---|---|
| Comp. Ex. V | 453.33 | 50.33 | 500.00 | 0.00 |
| Ex. XVI | 390.00 | 10.00 | 418.33 | 7.64 |
| Ex. XVII | 406.67 | 5.77 | 431.67 | 14.43 |
| Ex. XXI | 396.67 | 5.77 | 413.33 | 18.93 |
| Ex. XVIII | 410.00 | 10.00 | 478.33 | 7.64 |
| Ex. XIX | 403.33 | 5.77 | 506.67 | 11.55 |
| Ex. XX | 388.33 | 2.89 | 483.33 | 28.87 |

TABLE 18

Drainage Time (12 cycles) for Exemplary Liquid Hand Soaps

| Product | Drainage Time (hours:minute:seconds) (12 Cycles) | Standard Deviation |
|---|---|---|
| Comp. Ex. V | 0:06:44 | 0:02:49 |
| Ex. XVI | 0:06:28 | 0:01:07 |
| Ex. XVII | 0:07:01 | 0:00:06 |
| Ex. XXI | 0:09:15 | 0:02:17 |
| Ex. XVIII | 0:09:07 | 0:01:35 |
| Ex. XIX | 0:12:30 | 0:02:03 |
| Ex. XX | 0:08:24 | 0:02:34 |

Tables 12 through 18 describe the results of foam evaluation testing for exemplary body wash and liquid hand soap formulations comprising various alkyl polyglucoside surfactant systems (e.g., caprylyl/capryl glucoside alone, decyl glucoside alone and with differing ratios of a combination of caprylyl/capryl glucoside and decyl glucoside from 3.5:1 to 1:3.6). The higher the Flash foam (mL) and maximum foam height (mL) indicates a greater amount of foam. The longer the drainage timing, the more stable the foam. The flash foam testing and the drainage time testing both provide an overall foam profile. Varying the ratios of a combination of caprylyl/capryl glucoside and decyl glucoside from 3.5:1 to 1:3.6 results in providing the optimum ratios for foam profile.

Example 3: Prebiotic Bacteria Testing

Figure 1:
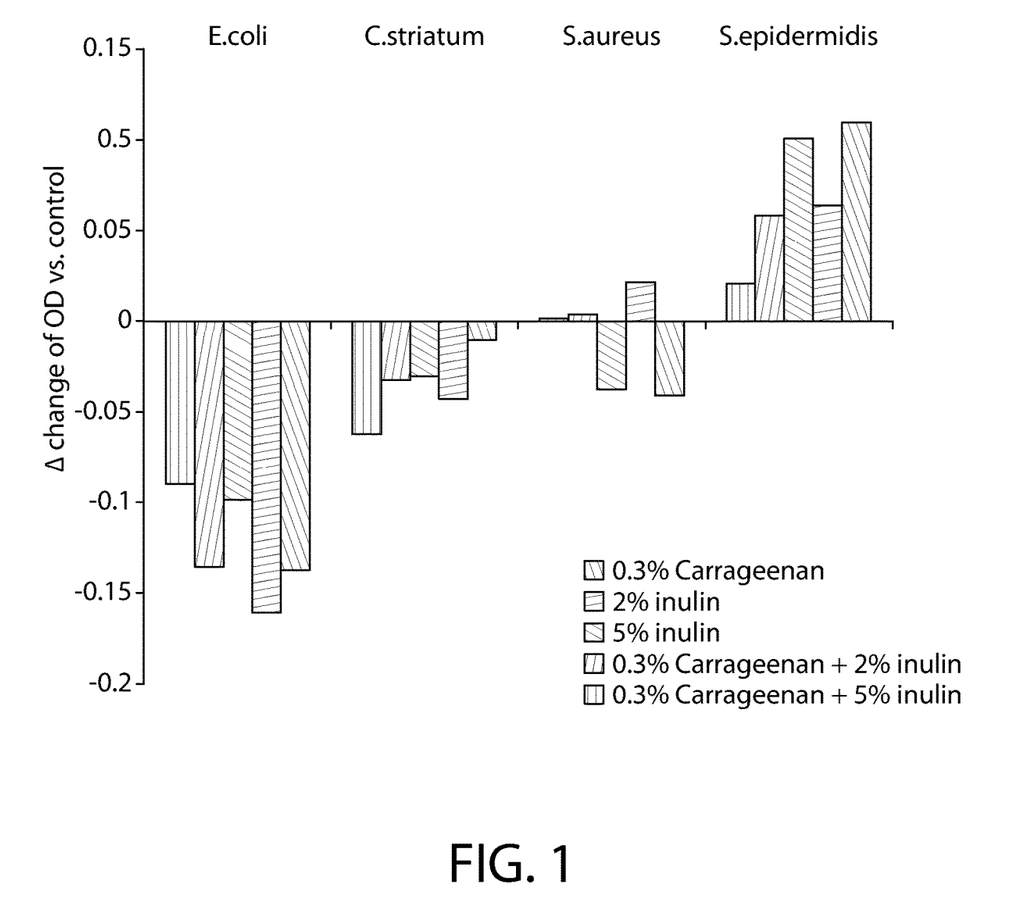
FIG. 1 depicts the selective inhibition of bacteria provided by certain prebiotic ingredients.

The prebiotic effect of neat ingredient, inulin and carrageenan and the combination of inulin and carrageenan were tested in vitro. The growth inhibition assay was conducted to test whether the neat prebiotic ingredient inhibits or promotes the growth of skin bacteria. A pure colony of *Escherichia coli, Corynebacterium striatum, Staphylococcus aureus* and *Staphylococcus epidermidis* were grown in Tryptic Soy Broth (TSB) medium overnight. The turbidity of the bacterial culture solution was adjusted to 0.1 OD (Optical Density) at 610 nm using a UV-VIS Spectrometer Lambda 45 from Perkin-Elmer. The neat ingredients were diluted into Tryptic Soy Broth (TSB) medium at certain concentration. 2 ml of the bacteria culture solution was incubated with 2 ml of 2% or 5% inulin or 0.3% of carrageenan at 37° C. for 24 hours. The bacteria that was incubated with the medium alone was considered the control. The turbidity of each tube was read after incubation at 610 nm using a UV-VIS Spectrometer. Replicates were run for each treatment. The average OD number of the prebiotics was subtracted by the number of the control. If the value is negative, the prebiotics inhibit bacteria growth, if the value is positive, the prebiotics promotes the growth of bacteria. The results showed 0.3% carrageenan, 2% and 5% inulin and the combination of carrageenan and inulin selectively inhibited the growth of undesirable bacteria (*E. coli C. striatum* and *S. aureus*) but promoted desirable bacteria (*S. epidermidis*) in vitro (see, e.g., FIG. 1).

Figure 2:
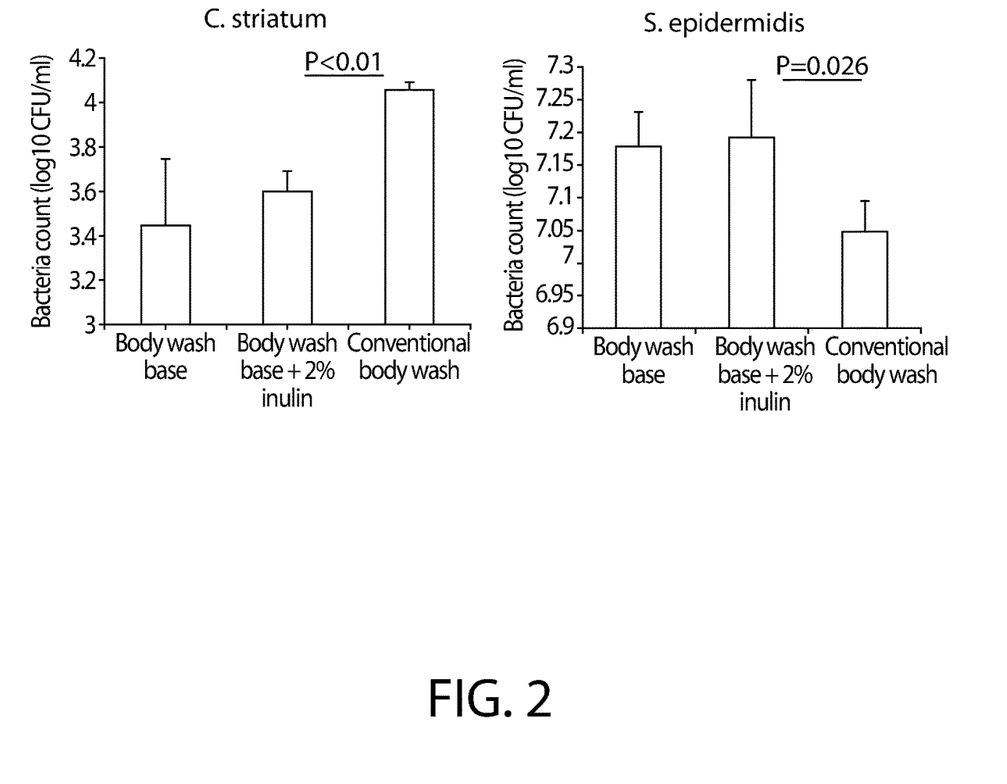
FIG. 2 depicts the selective inhibition of bacteria provided by an exemplary body wash of the present invention and a conventional body wash.

The prebiotic effect of a prototype body wash formula incorporated with prebiotics was also tested in vitro. A conventional competitive body wash was included as a control. 2% of inulin AGA was incorporated into body wash formula. The body wash was diluted to 1% solution in TSB medium. A pure colony of *C. striatum*, and *S. epidermidis* were grown in TSB medium overnight. The turbidity of the bacterial culture solution was adjusted to 0.10 D (Optical Density) at 610 nm using a UV-VIS Spectrometer. Then 2 ml of the bacteria culture solution was incubated with 2 ml of 1% body wash solution at 37° C. for 3 hours. After 3 hour incubation, the mixed solution was 10 times series diluted in TSB. 100 ul of bacteria solution was plated on Tryptic Soy Agar plates, and incubated at 37° C. overnight. The bacteria colonies on the plates were counted next day. The statistical significance of the numbers of bacteria colonies between treatments was analyzed by ANOVA at 95% confidence level in Minitab software. The results showed prototype body wash with 2% inulin showed prebiotic effect compared to a conventional body wash. It significantly increased the growth of desirable bacteria (*S. epidermidis*) and reduced undesirable bacteria (odor causing bacteria) compared to conventional body wash (Comp. Ex. II). (FIG. 2)

Example 4: Barrier Function Testing

Ex vivo skin benefit of prototype body wash with prebiotics was tested by external company Genoskin using NativeSkin®models. The skin biopsies collected from human donor during surgery were tape striped using 50 consecutive take strips (MonaDerm, DS100) prior to models production to remove stratum corneum. Models were cultured under cell culture conditions (37° C., 5% CO2 and maximum humidity) for either 3 days or 5 days with 1 mL standard Nativeskin® medium. 10 µL body wash was topically applied onto the skin surface in order for the compound to cover the whole surface in a homogeneous manner. Body wash samples were left in contact for 60 seconds and then rinsed off with Phosphate Buffered Saline (PBS). This procedure was repeated 3 times and models were finally rinsed 3 times at the end. Treatments were renewed every day. At day 3 and day 5, models are split into 2 batches, the skin tissues were processed for Lucifer yellow analysis, the rest were processed for histological analysis. 50 µL Lucifer Yellow at 1 mM was topically applied onto the skin models surface. Models were then incubated for 4 hours under cell culture conditions (at 37° C. in a C02 incubator with an atmosphere saturated with water). Lucifer yellow was then removed using a cotton swab, skin biopsies were fixed in 10% buffered formalin (e.g., HT501128 from Sigma Aldrich) for 48 hours and processed for paraffin wax embedding. The Lucifer yellow dye penetration indicates the skin barrier, the less dye penetration, the stronger skin barrier. Hematoxylin & Eosin staining was performed on 5 µm thickness paraffin-embedded skin cross-sections. For each sample, 3 transmitted-light pictures were acquired with a Leica DMil microscope with 40× magnification. The histological staining shows the integrity of skin structure.

Figure 3:
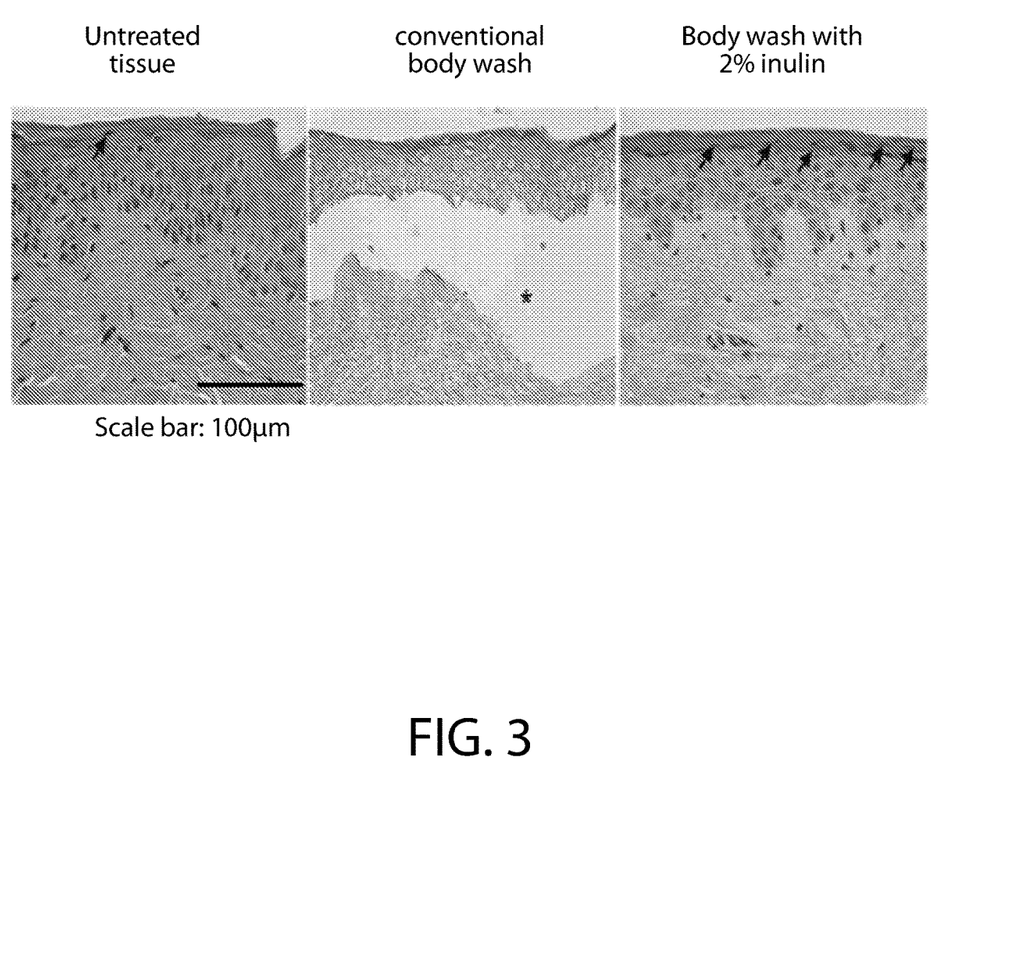
FIG. 3 depicts the results of barrier function testing conducted with an exemplary body wash of the present invention and a conventional body wash, in an ex vivo skin tissue model.

Ex vivo study showed the conventional body wash has strong negative effect on skin integrity and viability. At day 5, the skin structure of conventional body wash treated group was damaged, while prototype body wash with inulin maintained the skin normal structure, and the stratum corneum was regenerated after treatment (see, e.g., FIG. 3).

Figure 4:
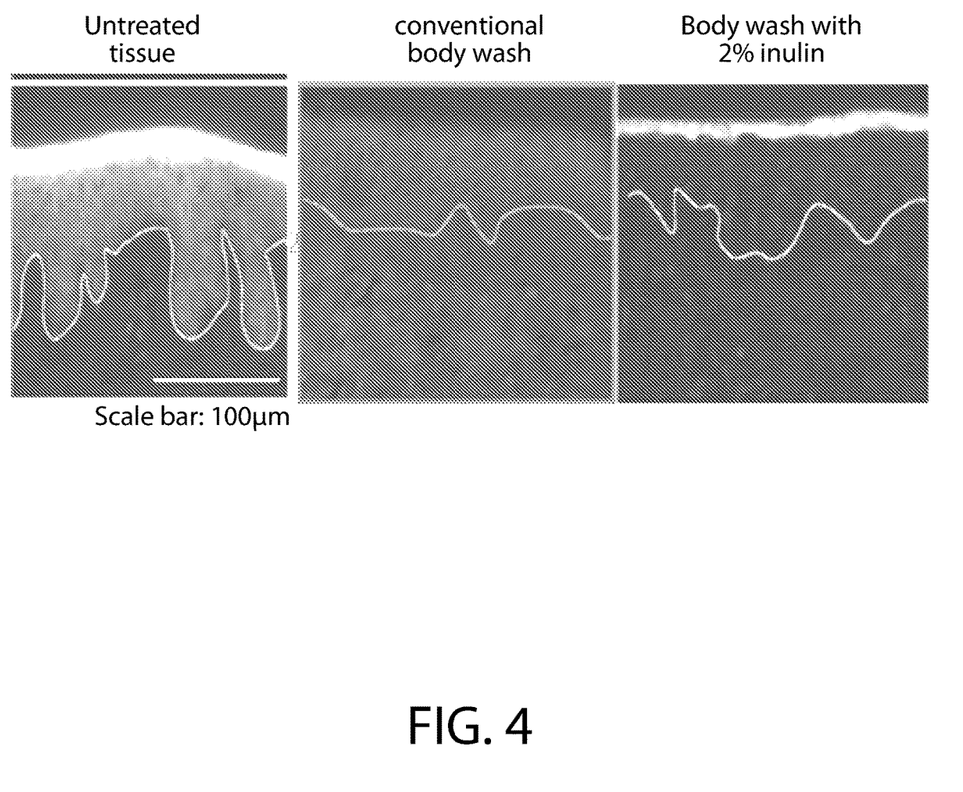
FIG. 4 depicts the results of a Lucifer yellow dye penetration assay for an exemplary body wash of the present invention and a conventional body wash.

The Luis yellow dye penetration assay showed, the skin tissue treated with prototype body wash with prebiotics has less dye penetration through epidermis, which indicated that the tissue treated with prototype prebiotics body wash has stronger skin barrier compared to conventional body wash (Comp. Ex. II) treated tissue and even untreated tissue (see, e.g., FIG. 4).

Example 5: Analysis of Alkyl Polyghteosides

Analysis of different alkyl polyglucosides (APG) carbon chain distributions of the raw materials as well as in finished products were used to determine the optimum ratio for the foaming profile. The carbon chain distribution of alkyl polyglucoside (APG) raw material was determined by an Agilent 1200 Series HPLC equipped with an Agilent 1290 Infinity II Evaporative Light Scattering Detector (ELSD) and also with a Agilent 1260 Infinity II HPLC equipped with a single quadruple mass spectrometer. The carbon chain homologs were separated using a Zorbax SB-C18 column (Agilent Part No. 863953-902) and also with an Agilent Eclipse Plus Phenyl Hexyl column (Agilent Part No. 959941-912) employing a reversed phase mobile phase gradient of 0.1% formic acid Water and 0.1% Formic acid Methanol. The ELSD parameters were 35° C. evaporator temperature/35° C. nebulizer temperature/1.6 L/minute nitrogen gas flow. The raw material sample concentration was 2.0 mg/mL in a diluent with 10% water and 90% methanol. Carbon chain homologs were identified by relative retention dynes and also by single ion monitoring on a single quadruple mass spectrometer. The expected order of elution is characterized according to the number of carbons in the alkyl. homologs: increased chain length resulting in longer retention times (Kuhn, "Characterization of Mixtures of Alkyl Polyglycosides (Plantacare) by Liquid Chromatography-Electrospray Ionization Quadrupole Time-of-Flight Mass Spectrometry", 2004, pp. 2347-2353).

Results were calculated by normalized area percent and indicated that decyl octyl glucoside raw material (Plantaren 810 UP) contained C8 and C10 homologs while decyl octyl lauryl glucoside raw materials (Plantaren 818 UP, Plantaren 2000N UP) contained C8, C10,C12 and C14 homologs.

What is claimed is:

1. A personal care composition comprising:
a gum system comprising a plurality of natural gums;
a surfactant system comprising a plurality of alkyl polyglucoside surfactants;
a prebiotic agent inulin; and
a cosmetically acceptable carrier;
wherein inulin is present in an amount of from 2 wt. % to 5 wt. % of the total weight of the composition;
wherein the plurality of alkyl polyglucoside surfactants are present in an amount of from 15 wt % to 25 wt % of the total weight of the composition, and
wherein the plurality of alkyl polyglucoside surfactants comprises a first alkyl polyglucoside surfactant and a second alkyl polyglucoside surfactant present in a weight ratio of from about 4:1 to about 2:1.

2. The personal care composition according to claim 1, wherein the natural gums are selected from: xanthan gum; carrageenan; agar; an alginate; gum arabic; gum ghatti; gum tragacanth; karaya gum; guar gum; locust bean gum; beta-glucan; dammar gum; glucomannan; psyllium seed husks; tara gum; and gellan gum.

3. The personal care composition according to claim 1, wherein the plurality of natural gums comprises: xanthan gum and carrageenan.

4. The personal care composition according to claim 1, wherein the gum system comprises from about 0.1 wt. % to about 3 wt. %, of the total weight of the composition.

5. The personal care composition according to claim 1, wherein the plurality of alkyl polyglucoside surfactants comprises about 22% of a mixture of Caprylyl/Capryl Glucoside (16.95%) and decyl glucoside (4.84%), based on the total weight of the composition.

6. The personal care composition according to claim 1, wherein the first alkyl polyglucoside surfactant and the second alkyl polyglucoside surfactant are present in a weight ratio of aboot 3.5.1.

7. The personal care composition according to claim 1, wherein the plurality of alkyl polyglucoside surfactants are selected from: decyl glucoside; caprylyl glucoside; capryl glucoside; lauryl glucoside; coco-glucoside; and mixtures thereof.

8. The personal care composition according to claim 1, wherein the plurality of alkyl polyglucoside surfactants comprises: decyl glucoside and caprylyl/capryl glucoside.

9. The personal care composition according to claim 1, further comprising an antioxidant selected from: vitamin A, niacinamide; vitamin C; vitamin E; a polyphenol; resveratrol; co-enzyme Q10; a flavonoid; and a combination of two or more thereof.

10. A personal care composition comprising:
a prebiotic agent inulin;
a surfactant system comprising a plurality of alkyl polyglucoside surfactants;
a polysaccharide gum; and
a cosmetically acceptable carrier;
wherein the plurality of alkyl polyglucoside surfactants are present in an amount of from 15 wt % to 25 wt % of the total weight of the composition; and
wherein the plurality of alkyl polyglucoside surfactants comprises a first alkyl polyglucoside surfactant and a second alkyl polyglucoside surfactant present in a weight ratio of from about 4.1 to about 2:1.

11. The personal care composition according to claim 10, wherein the polysaccharide gum is selected from: xanthan gum; carrageenan; guar gum; karaya gum; an alginate; and gum arabic.

12. The personal care composition according to claim 10, w ereir Arst alkyl polyglucoside surfactant and the second alkyl polyglucoside surfactant are present in a weight ratio of from about 3.5.1.

13. The personal care composition according to claim 12, wherein the alkyl polyglucoside surfactant is selected from: decyl glucoside; caprylyl glucoside; capryl glucoside; lauryl glucoside; coco-glucoside; and mixtures thereof.

14. A method for cleansing a keratinous surface of a subject in need thereof, comprising administering a personal care composition comprising:
a prebiotic agent inulin present in an amount of from 2 wt % to 5 wt. % of the total weight of the composition;
a gum system comprising a plurality of natural gums;
a surfactant system comprising a plurality of alkyl polyglucoside surfactants, wherein the plurality of alkyl polvalucoside surfactants are present in an amount of from 15 wt % to 25 wt. % of the total weight of the composition; and wherein the plurality of alkyl polyglucoside surfactants comprises a first alkyl polyglucoside surfact and a second alkyl polyglucoside surfactant present in a weight ratio of from about 4:1 to about 2:1; and
a cosmetically acceptable carrier;
to a keratinous surface of said subject.

15. The method according to claim 14, further comprising the step of rinsing the keratinous surface to remove at least a portion of the personal care composition.

16. The method according to claim 14, further comprising the step of rinsing the keratinous surface until the personal care composition is substantially removed therefrom.

17. The method according to any one of claims 14, wherein the keratinous surface is selected from: hair; skin; nails; and a combination of two or more thereof.

* * * * *